United States Patent [19]
McKaughan et al.

[11] Patent Number: 5,301,129
[45] Date of Patent: Apr. 5, 1994

[54] VIDEO WEB INSPECTION SYSTEM EMPLOYING FILTERING AND THRESHOLDING TO DETERMINE SURFACE ANOMALIES

[75] Inventors: Stephen V. McKaughan, Arlington; Gary F. Nevers, Lynn; Joseph W. Landry, Saugus; John P. Fallon, Andover, all of Mass.; Paul R. Adomaitis, Trafford, Pa.

[73] Assignee: Aluminum Company of America, Pittsburgh, Pa.

[21] Appl. No.: 875,672

[22] Filed: Apr. 29, 1992

Related U.S. Application Data

[63] Continuation-in-part of Ser. No. 537,841, Jun. 13, 1990, abandoned.

[51] Int. Cl.$^5$ .............................................. G06F 11/00
[52] U.S. Cl. ..................................... 364/552; 364/469; 364/507; 364/572; 356/429; 356/430; 250/559; 250/571; 250/572
[58] Field of Search ............... 364/464, 470, 471, 472, 364/507, 552, 572; 356/429, 430, 431, 376; 358/101, 106; 250/559, 571, 572; 382/1, 22, 25

[56] References Cited

U.S. PATENT DOCUMENTS

| | | | |
|---|---|---|---|
| 4,675,730 | 6/1987 | Adomaitis et al. | 358/106 |
| 4,904,877 | 2/1990 | Pietzsch | 250/572 |
| 4,931,657 | 6/1990 | Houston et al. | 250/559 |
| 5,068,799 | 11/1991 | Jarrett, Jr. | 364/507 |
| 5,153,844 | 10/1992 | Beni et al. | 364/560 |

Primary Examiner—Kevin J. Teska
Assistant Examiner—Hal D. Wachsman
Attorney, Agent, or Firm—Elroy Strickland

[57] ABSTRACT

Method and apparatus for inspecting the surface of a moving web of homogeneous material for anomalies, the apparatus including a light source for illuminating the web surface and a light sensitive detector for receiving data from the web surface. The data is representative of the light reflected from the surface, as the light is affected by surface anomalies and background information. Computational means are provided for receiving output data from the detector in response to the data the detector receives from the web surface, and for processing the output data in a manner that determines the presence of surface anomalies. The computation means includes a plurality of filters for transforming the surface data in a manner that effects substantial elimination of the background information, and means for establishing threshold levels for background information. In addition, automatic means is provided for modifying the threshold levels in response to changes in the reflectance, frequency, or contrast of background information received by the detector and forwarded to the computation means.

11 Claims, 5 Drawing Sheets

VIDEO WEB INSPECTION SYSTEM EMPLOYING FILTERING AND THRESHOLDING TO DETERMINE SURFACE ANOMALIES

BACKGROUND OF THE INVENTION

This application is a continuation-in-part of application Ser. No. 537,841 filed Jun. 13, 1990, now abandoned.

The present invention relates to surface inspection of rapidly moving material. More particularly, the present invention relates to a method of detecting surface irregularities of moving webs of non-discreet, homogeneous material in a rapid, repeatable manner which is suitable for use in large industrial scale processes. The invention further relates to an apparatus for carrying out such a method.

Over the years, many industries have sought video inspection of materials for surface texture and/or surface anomalies. Video inspection has been used successfully in detecting defects in individual items where each item to be inspected, e.g., a semi-conductor wafer, is moved to an inspection location and stopped. Light is directed to the item and the pattern of light reflected, refracted, or transmitted is compared to information from a standard to determine whether the pattern is correct, or whether or not some surface irregularity exists.

Moving from a stop-and-start, relatively small scale, visual inspection system to an industrial size inspection system useful for rapidly moving non-discreet homogeneous materials has been exceptionally difficult. In cases where the material under test has substantial three-dimensional differences, the differences in illumination and inspection angle caused by changes in the geometry of the three-dimensional differences can cause a substantial false detection probability. The three-dimensional problem with discrete items is not as significant as that of continuous, or semi-continuous surfaces, such as metal plate, particularly if the surface is passing the inspection station at a rapid pace. Irregularities in and on the surface can cause substantial inaccuracies in two-dimensional (x-y) surface data. Further, in any large scale industrial process, such as metal or plastic manufacturing, there may be optical differences caused by surface wear in the handling equipment itself. Such wear, as in roll grind textures, can cause changes in transmission or reflection characteristics of the rolled item. This produces optical scattering that is reported (detected) as surface variations, and possibly as defects; such surface irregularities may be acceptable, however, and should not be classified as defects.

Further, the magnitude of wear-related changes can be substantial so as to mask actual surface defects unless some method is employed to remove these changes from the optical image of the surface.

Large scale industrial operations can lead to other problems due primarily to the size of the material under inspection and the environment in which it is used. For example, surface inspection systems employed to detect marks or other irregularities or variations on metal sheet may require identification and/or classification of many different types of marks, such marks ranging in size from several feet in either dimension down to marks as small as a few millionths of an inch, depending upon the resolution chosen for the task at hand. Marks are found on webs and strip ranging in size from 4 to 8 feet in width and move past an inspection site at rates of 60 miles per hour, with the web having, in addition, a continually changing reflectivity because of wear or grind patterns and buckling of the web. Detection problems under these conditions are much more difficult than inspecting small scale, cut-to-length items.

The problems of surface inspection of webs haven't been solved by standard systems such as laser-based visual inspection systems or upgrading systems used for inspecting discrete items. Therefore, a new technology has had to be developed.

SUMMARY OF THE INVENTION

The present invention is directed to a web inspection system and method that provides rapid, repeatable automatic surface variation detection and characterization of web surface properties. The inspection system has broad scale industrial applications and is particularly useful on many manufacturing processes involving bulk materials. By proper selection of apparatus and certain data processing techniques, minute irregularities on wide metal sheet moving at 5,000 feet per minute can be detected.

An objective of the invention, therefore, is to provide methods and apparatus for eliminating background information (noise) when inspecting webs of moving material in a direction perpendicular to the surface being inspected. Background information includes web buckle which can occur when traveling materials are unsupported at the detection location.

The web inspection system of the invention includes one or more light sources, such as strobed light sources, and at least one surface data acquisition device, preferably a light energy receiver and processor, such as a solid-state charge-coupled video camera. The camera is placed to receive light reflected from the web. A light source illuminates the web and the acquisition device (camera) receives light reflected by the web. The acquisition device provides data related to the surface condition of the web material. The inspection system further includes detection processors that are computational devices for processing image input data from the camera. The processors identify irregularities or anomalies on the surface of the web. The system also includes analog to digital converters and other hardware necessary to place the output of the camera in proper electronic format for entry into the processors.

As part of the processors, the web inspection system of the invention includes a series of multi-dimensional convolution filters for transforming the output of the camera in a manner that substantially eliminates background information while enhancing the features of anomalies to differentiate them from the background. Depending on the size of the defect, the preferred signal transformation detects the edge of a mark or acts as a template filter and provides a derivative of the resulting signal in a direction perpendicular to web movement, and integration of the signal in the direction of web movement. Such filtering has the net effect of locating changes in the web surface, e.g., edge effects and light-dark transitions in light intensity in a direction transverse to web movement while summing the light intensity in the direction parallel to web movement. The multi-dimensional filtering is preferably implemented in recursive forms for computational efficiency.

The web inspection system of the invention is also directed to elucidating and processing the information obtained from the camera, including the use of a first background threshold, the level of which is set so that integrated input data from the camera is a constant, using a closed-loop feedback system that provides statistically stable data.

A second threshold is applied to information passing the first threshold and is set by predicting where the statistically stable data would normally reach zero population density. Any data exceeding these thresholds is abnormal or, in all likelihood, a defect (anomaly). Both threshold levels are automatically adjusted in response to modifications in input signals from the camera, the second threshold being adjusted in response to changes in the first background threshold.

Automatic modification of the thresholds is needed, as grind marks and other miscellaneous changes occurring in a roll surface, are reproduced on the web surface. In addition, three-dimensional changes such as buckle in the web are not sensed by the convolution filters, as the filters have a frequency response that is basically high-pass, the filters being finite impulse response filters that simulate the taking of the second derivative of the camera image in a cross-wise direction. The buckle has low frequency edges (intensity gradients) that produce a signal lower than normal background.

For inspection of highly reflective surfaces, e.g., aluminum or steel, at least two video cameras are preferred, one located relative to the light source and the web to provide specular or bright field data and the other located to provide diffuse or dark field data. The light paths between the light source, the web and the video cameras are interruptible on a controllable, periodic basis to provide a stationary image. This can be accomplished either by placing a shutter in the light path or more preferably, using a strobed light source.

The preferred acquisition device for use in the method of the invention is a matrix array video camera, as discussed above, whereby a kernel of data constitutes an array of video signals related to distinct locations in the field of view of the camera. In preferred operation, the array is formed into subframes, the integrated intensity of the region is calculated, and the subframe tested again in a threshold based on a probability density function. The above second threshold value is applied to this intensity/probability density function to identify subframes containing anomalies.

BRIEF DESCRIPTION OF THE DRAWINGS

The invention will be better understood from the following detailed and accompanying drawings in which.

DETAILED DESCRIPTION OF THE INVENTION

Figure 1:
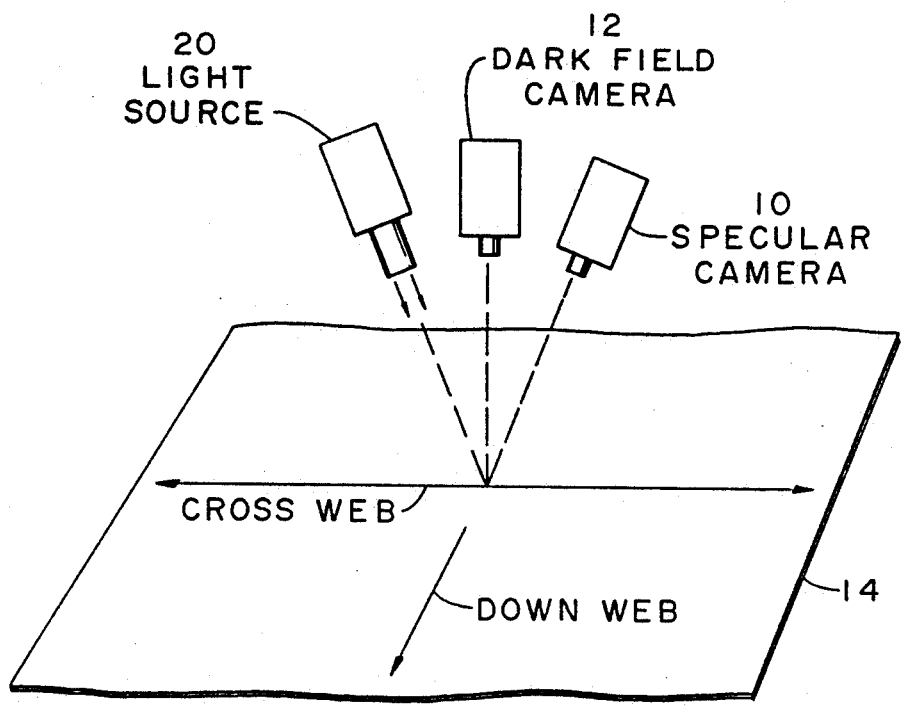
FIG. 1 is a schematic illustration of two video cameras located in relation to a web of material for carrying out the purposes of the invention.

Referring now to FIG. 1 of the drawings, two cameras 10 and 12 are shown diagrammatically for inspecting a web 14 of light reflective metal, e.g., aluminum sheet, moving at a speed as great as 60 miles per hour. A strobe light 20 can be used as a web illuminating source to arrest images of the web surface. The strobe is set at a suitable angle, depending on the specular properties of the material under investigation. In lieu of a strobe, a pinwheel or shutter mechanism can be used in front of the light source or the cameras to provide stationary images.

Fresnel lenses may be used in the illumination path to optimize the surface illumination. Fresnel lenses achieve this inexpensively in comparison to oval shaped glass lenses.

Preferably, the cameras are solid-state devices, such as charge coupled video cameras, that receive reflected light in acquiring surface data from web 14. The cameras acquire the data and present the same in rows and columns of solid-state elements (picture elements or pixels). Camera 12 receives dark field reflection while camera 10 is used to receive specular reflection. The cameras are located at distances from the web that provide a proper field of view for each camera.

Figure 2:
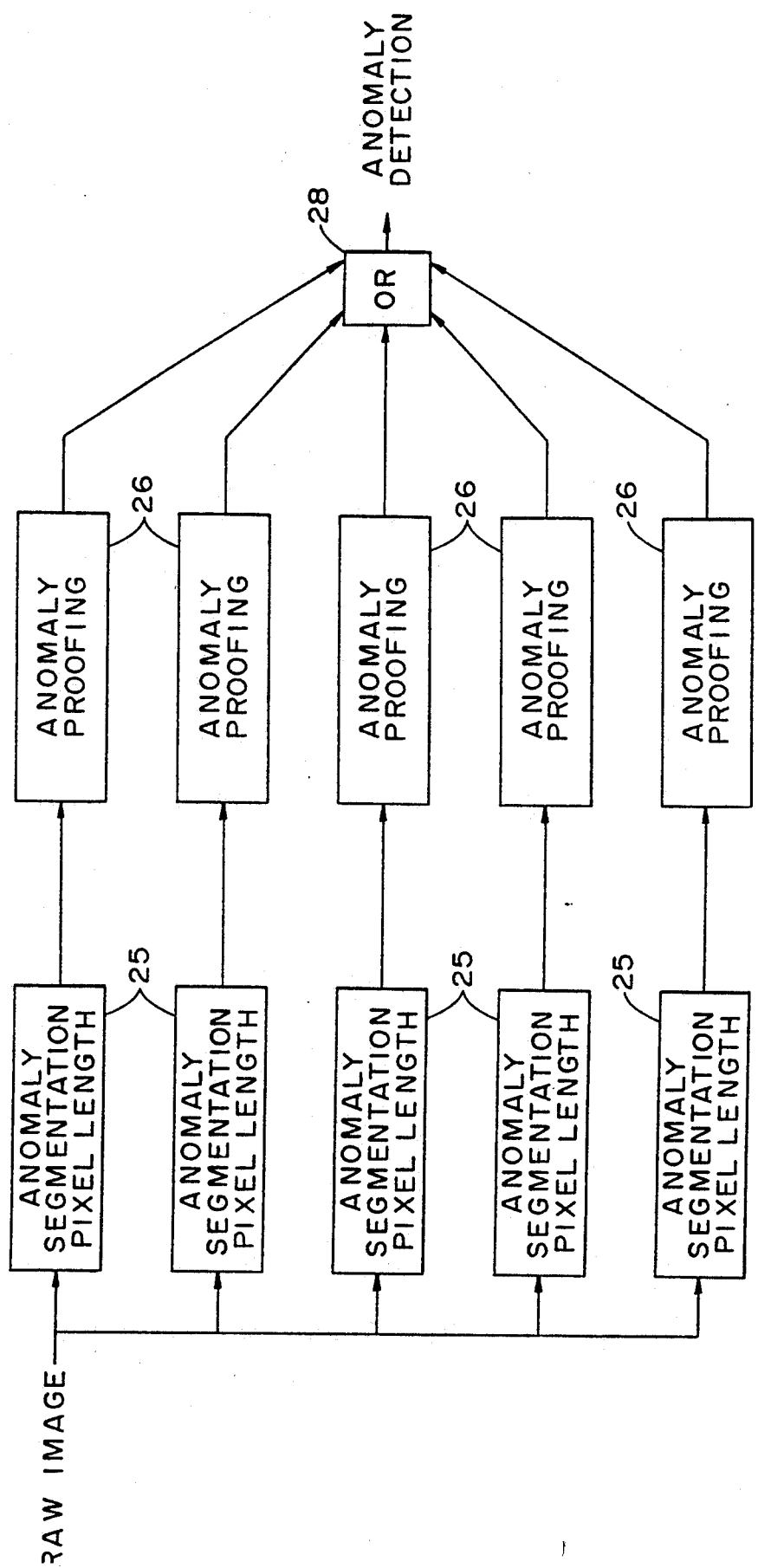
FIG. 2 is a flow diagram showing five of ten data paths handling the output from one of the two cameras of FIG. 1, and showing generally the processing steps of the invention.

Cameras 10 and 12 each produce a signal output that is electrically conducted to filter processors 25 (FIG. 2) that provide mark segmentation by identifying marks according to their length in pixels. A pixel value is selected to be one-half the size of the smallest unwanted mark or other anomaly to be detected. In the case of $6 \times 4\frac{1}{2}$ inch field of view, a $0.020 \times 0.020$ inch mark, which corresponds to slightly more than 2 pixels horizontally by slightly less than 2 pixels vertically, 4 pixels fits the mark. Other values can be selected by varying the field of view to match the size of the anomalies to be segregated. The best filter for detecting small features is a $10 \times 2$ filter, the template matching aspects of the filter being the most prominent. The first box 25 in FIG. 2, for example, represents a filter that processes marks that are say two pixels in length. The other processors shown in FIG. 2 represent filters for processing marks of increasingly greater lengths upon receiving information from one of the cameras. A similar set of processors is used for signals from other cameras.

The detection algorithm of the subject invention was developed for the following types of features (anomalies), namely, (1) long, narrow features orientated in a down web direction; typical features of this nature are scratches; (2) small $2 \times 2$ pixel symmetrical features such as marks that are repetitively placed on a web by the work rolls of a mill; (3) large features that may or may not be fixed symmetrical, lubricant stains are typical of this type; and (4) long, broad features such as elongated bands that are down web orientated and may extend for hundreds of feet.

If the sheet being inspected is unsupported at the location of inspection and has center and/or edge buckles caused by stresses in the material that distort its flatness, the result is that the buckle areas reflect light outside the acceptance angle of the camera lens. Therefore, buckle results in dark areas in the image. These areas are irregular in shape and change from image to image. The algorithm of the invention is specifically designed to ignore the presence of buckle and to detect features outside the buckle area when and while buckle is present.

The operating scenario of the algorithm is based upon available data throughout the process. Certain "facts" were found that influenced the development of the algorithm and had a major influence upon the setting of thresholds for segmentation of surface marks. For example, the grind patterns of work rolls in rolling aluminum sheet do not change significantly in the rolling of a large coil of the sheet in the down web direction but may change significantly in the cross web direction. Therefore, the background signals obtained by the cameras and the processors from "good" or acceptable sheet moving in the travel direction of the sheet are relatively constant. However, in the case where cameras traverse the strip to sample and inspect or when using a plurality of cameras to cover the sheet width, different thresholds are required based upon the data of the respective scenes. Also, the roll grind pattern can differ from one mill to another or from one set of work rolls to another. In practice, background signals vary by as much as 35% between rolls and mills.

Secondly, features that signify defects or anomalies occur very seldom. For example, in a line speed of 1,000 feet per minute, a repetitive roll mark with a period of 24 inches is observed in 19% of the acquired images. If the sheet is 88 inches wide and fully scanned, the role mark would comprise less than 0.04% of the images. Estimates of random features, which might occur 1% of the time, yield possible occurrences in approximately 0.02% of the images.

The outgrowth of the above is that thresholds applied to the processes of the algorithm must be automatically adaptive and that once the correct threshold is reached it will not change rapidly or significantly.

FIG. 2 shows generally the processes of the invention in which segmenting (boxes 25) of marks of different lengths takes place and proofing of the length data (boxes 26). Segmenting is preferably a recursive filtering process using a series of real-time image convolution operations on each kernel of input data from each camera.

Proofing at 26 involves differentiation of potential unwanted marks from the background of sheet 14, all of which will be explained in detail in connection with the flow chart of FIG. 3. The results of segmenting and proofing are directed to an OR process at 28. The process outputs a signal whenever any one or more of the proofing operations indicates there is an anomaly or other unwanted mark or foreign matter on the surface of web 14. Such a mark or anomaly would include a water spot, for example, remaining on a surface of a strip, the spot being the result of coolant applied to the rolls and/or roll bite of a mill reducing the thickness of the strip, and not properly evaporated from the surface.

Certain strip conditions produce significant intensity variations but are not considered detrimental to the final use of the product. Additionally, they occur so frequently that the system must ignore them initially rather than separate their data from other defects at a later time. Buckle is an anomaly of this type. Thus, the system must compensate for variations in roll grind pattern while eliminating known anomalies of a specific nature. Such compensations are described in the following sequential operations.

Figure 3:
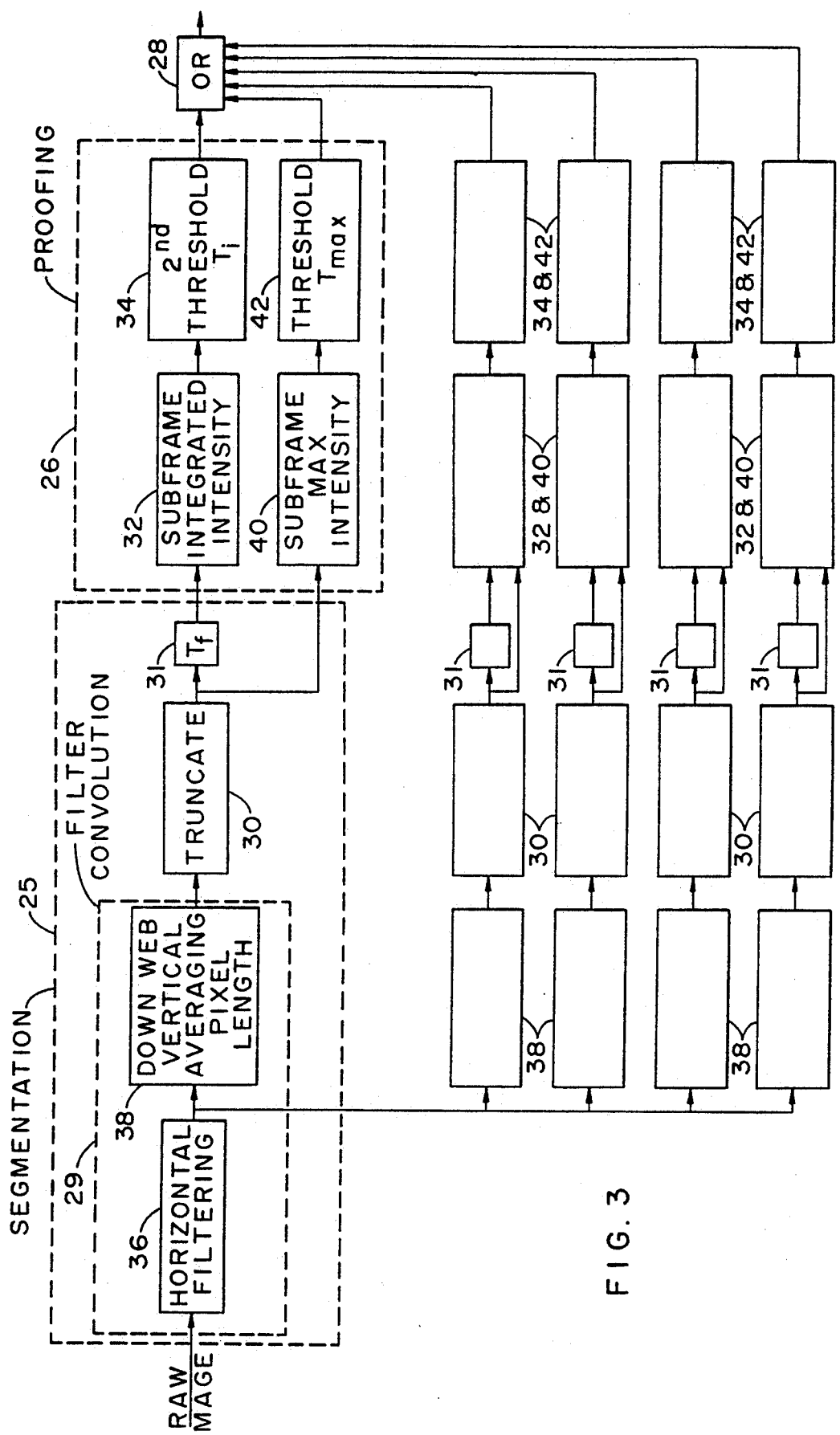
FIG. 3 shows in some detail one of the data paths depicted in FIG. 2.

The first, as shown in FIG. 3, is the segmentation function, indicated generally by large box at 25. This function includes image (filter) convolution (box 29 located within box 25), as discussed below. The segmentation function also includes data compression at 30 and an initial thresholding operation at 31.

The next general function is image proofing at 26, which includes integrating subframe intensity at 32, and a second thresholding at 34.

Each image from cameras 10 and 12 is convolved with up to 5 two-dimensional filters in a two-step operation. Image convolution is the operation of the filters shown at 36 and 38 in FIG. 3. The convolution is performed on each pixel in the image beginning at the top left corner of the image and moves horizontally across the image. At the end of the row or line of pixels, the sequence is repeated until the end of the bottom line of the camera raster is reached. Horizontal filtering at 36 acts as a template filter for small marks and as an edge detector for larger marks. Typical filter constants in the horizontal filter are:

$$1\ \ 1\ \ 0\ \ 0\ \ -2\ \ -2\ \ 0\ \ 0\ \ 1\ \ 1$$

The marks that match the template best lie in the range of 2 pixels wide to 6 pixels wide. Large scale signals are provided for narrow marks that are lighter or darker than the background. Small signals occur for edges of larger marks. The filter effectively takes the second derivative of the image in the horizontal direction. The output of one horizontal filter is fed into five vertical filters.

The vertical filters integrate or average in the vertical direction (at 38), thereby building up the anomaly features that are correlated vertically in the image. The length over which the filters average is matched to the length of the potential defects for optimum performance. Averaging the image recursively reduces the computer hardware that would otherwise be needed. Recursive averaging is a continuous process whereby a sequence of values are scaled and added to the prescaled result. The scaling factors applied determine the weighting given to previous values in the sequence. An example of the operation would be adding 9/10 of a result to 1/10 of a new number to obtain the recursive average. The output of a recursive process can be described by the following formula:

$$Y(t) = \sum_{N=t}^{0} \frac{(N-1)^{t-N}}{N^{(t-N+1)}} X(N) \tag{1}$$

where N=number of values averaged.

The best combination of filters for detecting small marks is a 10×2 filter, the template matching aspects of the filter being the most prominent. For larger, narrow, or wide marks, the best combination would be a 10×32.

The number of filters employed depends upon the number of different anomaly sizes sought to be detected. Hence, in the case where only one size is sought, only one circuit and process 38 is needed.

Once the convolution has been performed on each image, the data is compressed at 30 by truncating (removing) the negative portion of a derivative of each signal from 38. A thresholding process $T_f$ at 31 is applied to the convoled, truncated image, which operates to separate potential defects from the background of the web surface and establish statistically reliable data for selecting the $T_i$ threshold, as discussed in detail hereinafter. This background thresholding provides data compression prior to an integrated intensity computation at 32 and is set at a level to eliminate known background data while retaining suspect and known anomaly data. Some of the suspect data are background signals and will be eliminated after further processing.

The following equation is employed for setting $T_f$:

$$k = N_1(L_1 - T_f) + N_2(L_2 - T_f) \ldots N_n(L_n - T_f) \quad (2)$$

where:

k is a constant value for integrated intensity,

N is the number of pixels at a given filtered intensity, and L is a given filtered intensity.

The filtered intensity data can be accumulated in histogram form, from which possible values of k for different thresholds are computed. The correct value for $T_f$ would then be selected when the computed k is within acceptable limits of the idealized k.

Figure 5:
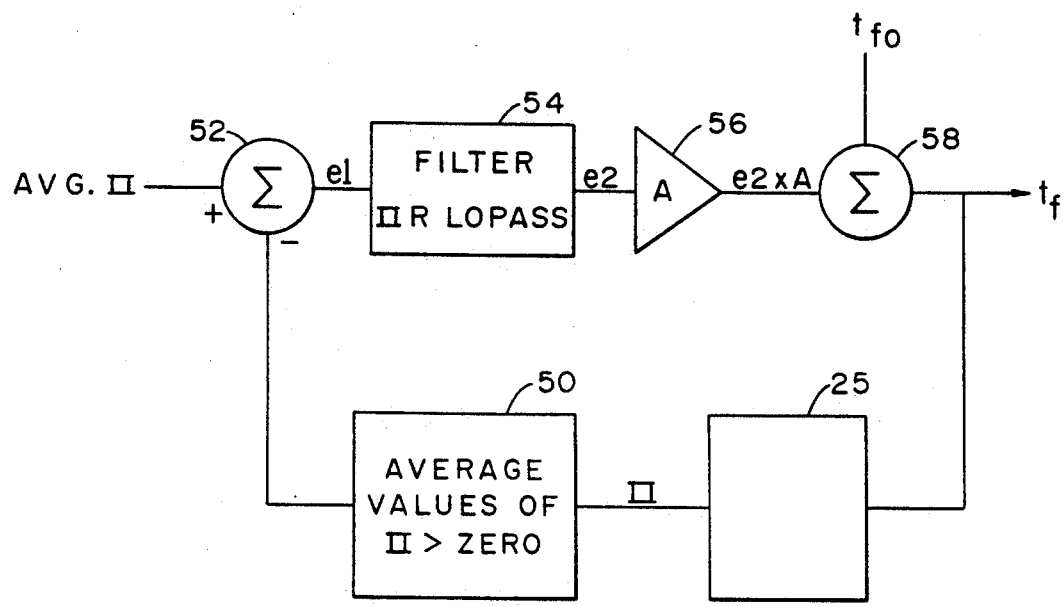
FIG. 5 is a flow diagram showing a process for updating a first threshold $T_f$.
Figure 6:
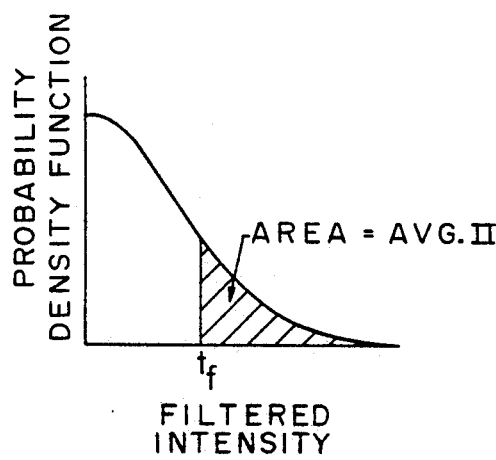
FIG. 6 is a graph showing the calculation of $T_f$.
Figure 7:
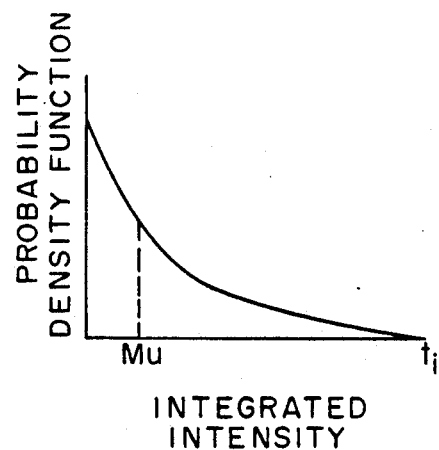
FIG. 7 is a graph showing the calculation of a second threshold $T_i$.

The setting of threshold levels in the present invention are based upon calculating various moments of the respective probability density functions, the underlying assumption being that the functions are either Gaussian or truncated Gaussians, as shown in FIG. 6. The level of threshold $T_f$ is a controlled input to the processes of the invention such that the level is set in a closed loop system, as shown in FIG. 5, in order to maintain stable operation of the processor and ensure optimal feature detection. The goal setting of $T_f$ is not only to optimize feature extraction but to ensure that the resulting integrated intensity function performed after the application of $T_f$ has a predictable characteristic, which causes a calculation of a second threshold level $T_i$ (FIG. 7) to also be stable and reliable.

$T_f$ is chosen such that the resulting area under the Gaussian distribution above $T_f$ is a constant, see shaded area in FIG. 6. It is equivalent to presetting the area above $T_f$ in the intensity versus probability density function. Hence, the closed loop routine of FIG. 5 can be viewed as a dynamic moment generating system.

The operation of the system of FIG. 5 is an updating algorithm in which the integrated intensities (II) are averaged at 50 for all subframes whose integrated intensities exceed zero. The average values are compared at 52 with the target average integrated intensity constant of FIG. 6 (AVG II) to produce an signal error e1 if there is a difference between the two. This signal is recursively averaged at 54 to form a second signal error e2. Error signal e2 is then multiplied at 56 by the gain of the loop of FIG. 5, which product is added at 58 to the original value $T_{fo}$ of the threshold to form a new, updated $T_f$ value.

Once the background threshold is set and operative at 31, all features whose filtered intensity exceeds $T_f$ in say at least four continuous pixels are deemed suspect. For most potential anomalies, the majority of the pixels will exceed the threshold $T_f$.

However, $T_f$ cannot be used as the sole discriminating factor because background noise may also exceed $T_f$ and change over time. In order to eliminate this problem, each image is broken into a number of smaller regions called subframes at 32. $T_f$ is subtracted from all of the pixel intensities within a subframe. All the resulting values at 31 are then summed within the boundary of the subframe at 32, thereby providing an integrated intensity value. If the integrated intensity of the subframe exceeds a second threshold value, which is the integrated intensity threshold $T_i$ at 34, the region is deemed to contain an unwanted mark.

An optimum subframe size for the defect population of interest in inspection of typical metals is 16×32 pixels. If a subframe is too small, large low contrast defects would have integrated intensities too low to be detected. The subframe size is, therefore, intentionally large to provide optimum integrated intensities for surface scratches that are narrow and long but of very low contrast. With a small subframe size, such long scratches would not be detected.

The present invention employs an algorithm for setting $T_i$ based upon several assumptions. These assumptions are (1) that if all of the material is "good" and the material grind pattern is constant, the distribution values computed for integrated intensity will be constant; (2) that the shape of a distribution curve of the values and their moments will vary from material to material; and (3) if 2 above is true, $T_i$ must be adaptive to the varying material surfaces.

Threshold ($T_i$) provides separation between background noise and anomaly features in those regions where potential marks have been identified. $T_i$ would be relatively easy to calculate if the background and anomaly distributions are separate, i.e., if there is no overlap of background and mark distributions (in FIG. 4 of the drawings there is some overlap). If there is no overlap, $T_i$ could be set at 34 to zero (N=0), N being the number of samples of a particular integrated intensity, in this case a value slightly higher than the background.

Figure 4:
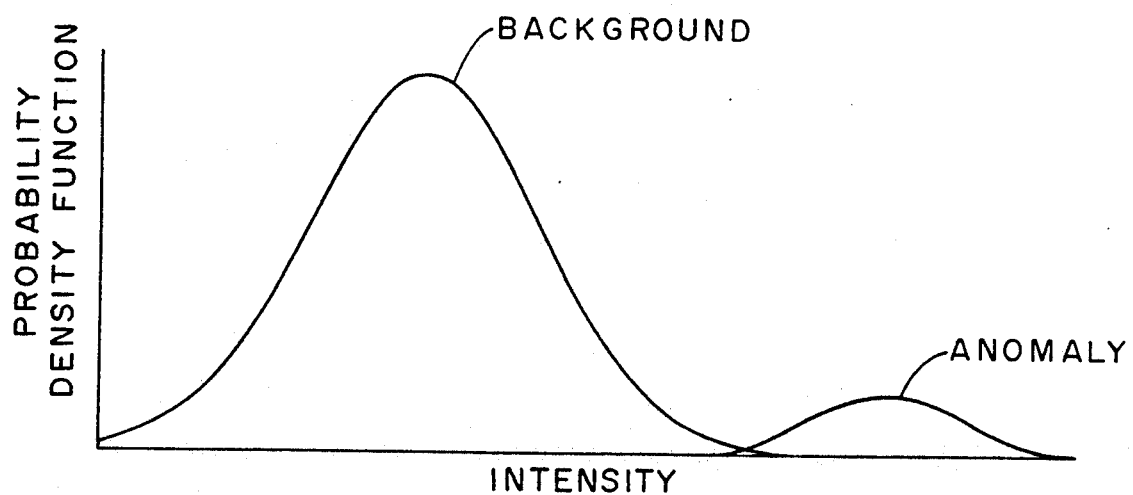
FIG. 4 is a graph showing the separation between background and anomaly data, as provided by filters employed in the invention.

The algorithm for setting $T_i$ is based on computing the point on the distribution curve where background signals reach zero whether background and anomaly distributions overlap or not, see FIG. 4. Having set the first threshold $T_f$ so that average integrated intensity (AVG II) is constant, the integrated intensity distribution values are relatively constant. Therefore, by finding the value of an integrated intensity that corresponds to say 1% population and multiplying this value by a constant, the value of $T_i$ is determined.

Figure 8:
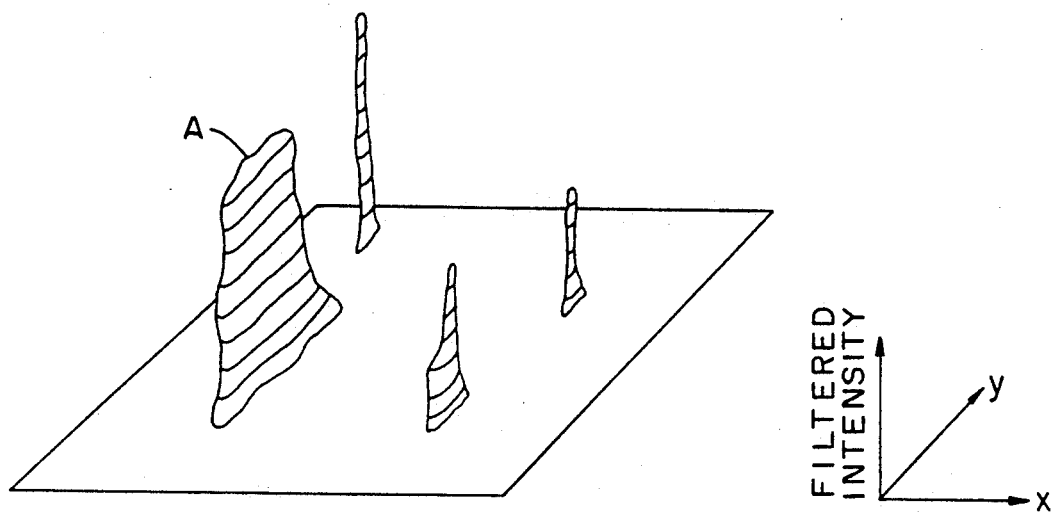
FIG. 8 is a three-dimensional spatial plot of pixel intensities in a hypothetical subframe.
Figure 9:
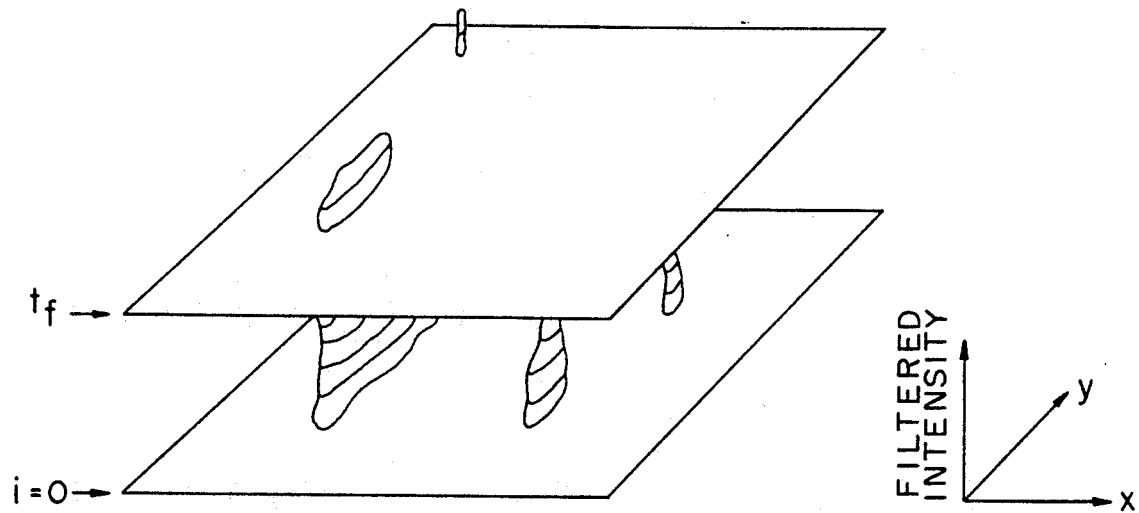
FIG. 9 is the plot of FIG. 8 showing a first threshold $(T_f)$ applied to the data in FIG. 8.

FIG. 8 is a three-dimensional spacial plot of pixel intensities in a hypothetical subframe. The intensity is plotted along the z-axis. A typical anomaly is shown by the designation "A"; all other elements in the figure are background noise which $T_f$ is set to eliminate, i.e., the application of threshold $T_f$ to the image eliminates those areas of the image that are known to be background simply by the strength of their signals. FIG. 9 depicts the plot of FIG. 8 with the threshold $T_f$ applied. Thereafter, the proofing algorithm of 26 becomes a simple measure of the volume of the intensity left over after $T_f$ is applied.

In most instances, the integrated intensity of the subframes is particularly helpful in identifying anomalies which are best matched in size to large kernel recursive filters. However, for small anomalies, subframe integration does not always assist the process. Therefore, the output data from the image convolution of these small filters is also analyzed (at 40) for the highest intensity pixel in a subframe, as labelled "subframe maximum intensity" in FIG. 3, wherein the maximum intensity for thresholding ($T_{max}$) is calculated and applied at 42. Thus, very small, single pixel defects with significant contrast may be detected, as well as those being 2×2 pixels.

As in all of the above examples involving changes in surface background and for the same reasons, threshold $T_{max}$ must be adaptable. The process by which this threshold is made adaptable is identical to that described above in connection with the calculation of $T_i$, except that the variable is filtered intensity rather than integrated intensity and the data is not truncated by $T_f$.

In all cases, background changes must be accounted for; otherwise, either anomaly detection probability will deteriorate or there will be a higher than acceptable false alarm rate. False alarms are those frames which the processors say contain an anomaly but upon further review do not contain an anomaly. Continual iteration of $T_i$ and $T_f$ based on changes in intensity at 32 and, accordingly, intensity thresholding at 34, holds errors in detection to a minimum.

While the invention has been described in terms of preferred embodiments, the claims appended hereto are intended to encompass all embodiments which fall within the spirit of the invention.

What is claimed is:

1. In an inspection system for repeatedly and automatically determining the existence of anomalies on a surface of a moving web of non-discrete, homogeneous material, said anomalies existing in the presence of a web surface background that is not anomalous, the system comprising:

a light source for illuminating the web surface;

a light sensitive device for acquiring data from the web surface, and for producing an image of said surface data in the form of pixel elements, and for providing output data that is representative of the web surface data acquired by the light sensitive device, and surface data being representative of the light reflected from the surface to the light sensitive device, as the light is affected by surface anomalies; and computational means for receiving the output data from said light sensitive device in response to the data said light sensitive device receives from the web surface, and for processing said output data in a manner that determines the presence of surface anomalies, said computational means including:

a plurality of multi-directional filters for transforming the web surface data in a manner that effects identification of web surface anomalies of different sizes and shapes and segregates the anomalies of different sizes and shapes from each other and from the web surface background by using edge detection or template matching of an anomaly and integration of anomaly length in the direction of web movement, said filters producing an output that is representative of said pixel elements;

means for establishing a threshold and applying the threshold to the output of said filters in a manner that separates the web surface background in the pixel elements from the web surface data in the pixel elements representing suspect and known anomalies; and means for dividing the image of the web surface data provided by the light sensitive device into subframes, the subframes containing pixel elements of varying intensities; and means for summing the varying intensities of the pixel elements within a subframe boundary in the direction of web travel to provide an integrated intensity value;

said integrated intensity value being indicative of the existence or non-existence of one or more surface anomalies.

2. The web inspection system of claim 1 including means for automatically modifying said threshold in response to changes in the web surface background received from the light sensitive device.

3. The web inspection system of claim 1 in which the light sensitive device comprises at least two video cameras, said cameras being located relative to the light source and web in a manner that enables the capture of specular reflection data and diffuse data from the web surface.

4. The web inspection system of claim 1 including:
means for providing a threshold value for said integrated intensity value whereby any features within the subframes exceeding said threshold are deemed to contain an unwanted anomaly.

5. The inspection system of claim 1 including:
means for calculating the highest intensity pixel element of a subframe;
means for applying a threshold to said calculated highest intensity pixel element; and
means for automatically modifying said threshold in response to changes in the web surface background.

6. A method of repeatedly and automatically determining the existence of anomalies on a surface of a moving web of non-discrete, homogeneous material, said anomalies existing in the presence of a web surface background that is not anomalous, the method comprising:

illuminating the surface of said web material;

locating a light sensitive detector to receive light reflected from said web surface in response to said illumination, said detector providing an image of the web surface in the form of pixel elements having values that represent web surface data of the moving web of material;

identifying anomalies that may exist on said web surface, and segregating anomalies of different sizes and shapes from each other and from the web surface background by subjecting said pixel element values to a series of computations that employ a plurality of multi-directional filters to effect edge detection or template matching of anomalies and integration of anomaly lengths in the direction of web travel, said filters providing an output that represents pixel element values having varying intensities;

providing a first threshold value and applying the first threshold value to the output of said filters in a manner that separates the web surface background from the web surface data representing anomalies; and dividing the image into subframes that have varying intensities;

summing the varying intensities of said subframes to provide an integrated intensity value;

using said integrated intensity value to determine whether or not an anomaly exists on the web surface; and automatically modifying the first threshold value in response to changes in the level of the web surface background received from the light sensitive device.

7. The method of claim 6 including changing said threshold value in response to changes in the web surface background.

8. The method of claim 6 whereby the computations are carried out by the steps of:

obtaining a kernel of signal data from the detector;
filtering said kernel of signal data;
obtaining data from said filtering step; and
applying the first threshold value to data obtained from the filtering step.

9. The method of claim 6 including:
using said detector to provide arrays of video signal values;
forming said arrays of signal values into the subframes having varying intensity;
integrating the intensity within each of said subframes;
providing a second threshold value; and
applying the second threshold value to said integrated intensities to identify subframes containing surface anomalies.

10. The method of claim 6 including:
selecting a threshold that maintains a constant average integrated intensity for all data obtained from areas containing no anomalies.

11. The method of claim 6 in which the moving web of material is unsupported in the vicinity in which the web surface is illuminated.

* * * * *